United States Patent [19]

Winant et al.

[11] Patent Number: 5,118,790
[45] Date of Patent: Jun. 2, 1992

[54] ANALOGS OF HIRUDIN

[75] Inventors: Richard C. Winant, Palo Alto; Jerome B. Lazar, Sunnyvale; Paul H. Johnson, Menlo Park, all of Calif.

[73] Assignee: SRI International, Menlo Park, Calif.

[21] Appl. No.: 557,514

[22] Filed: Jul. 24, 1990

[51] Int. Cl.$^5$ ................................. C07K 7/10
[52] U.S. Cl. ................... 530/324; 435/69.2; 530/855; 514/12
[58] Field of Search ................ 530/324, 855; 514/12; 435/69.2

[56] References Cited

U.S. PATENT DOCUMENTS

| 4,668,662 | 5/1987 | Tripier et al. | 514/12 |
| 4,745,177 | 5/1988 | Fritz et al. | 530/324 |
| 4,767,742 | 8/1988 | Dodt et al. | 514/12 |
| 4,897,348 | 1/1990 | Johnson et al. | 435/69.1 |

FOREIGN PATENT DOCUMENTS 273800 7/1988 European Pat. Off. .

OTHER PUBLICATIONS

Scharf et al., (1989) *FEBS Lett 255*:105.
Johnson et al., (1989) *Seminars in Thrombosis and Hemostasis 15(3)*.
Chang (1983) *FEBS Lett 164*:307.
Stone and Hofsteenage (1986) *Biochem 25*:4622.
Dodt et al. (1988) *FEBS Lett 229*:87.
Degryse et al., (1989) *Protein Engineering 2(6)*: 459.
Hofsteenage et al., (1990) *Eur. J. Biochem 188*:55.
Winant et al., *Biochemistry* (1991) 30(5):1271–1277.
Lazar et al., *Journal of Biochemistry* (1991) 266(2):685–688.
Product Bulletin from SRI International, 333 Ravenswood Avenue, Menlo Park, Calif. entitled "Real-Time Detection and Monitoring of Blood Coagulation" 1 page total.

*Primary Examiner*—Robert A. Wax
*Assistant Examiner*—Gabriele E. Bugaisky
*Attorney, Agent, or Firm*—Richard P. Lange

[57] ABSTRACT

Compounds and compositions comprising amino acid substituted and chemically modified analogs of hirudin are provided, together with methods for their production and use as antithrombotic and anticoagulant agents.

13 Claims, 5 Drawing Sheets

ANALOGS OF HIRUDIN

TECHNICAL FIELD

The present invention relates generally to analogs of hirudin polypeptides and more particularly, to chemically modified, amino acid substituted hirudin polypeptides, together with methods for their production and use.

BACKGROUND OF THE INVENTION

Hirudin is a small protein isolated from the salivary glands of the medicinal leech, *Hirudo medicinalis*. It is the most potent and most specific known inhibitor of thrombin, the serine protease that functions in regulating hemostasis and that catalyzes the final step in blood coagulation—the conversion of fibrinogen to clottable fibrin. Hirudin has been shown to be an effective anticoagulant and antithrombotic agent in animals and humans and may be uniquely suited to the clinical treatment of venous and arterial thrombosis—particularly as an adjunct to fibrinolytic therapy, disseminated intravascular coagulation, antithrombin-III deficiency, the control of fibrin deposition during wound healing, and some forms of metastatic cancer.

The purification and characterization of hirudin from the leech have been well-studied. The primary structures of three variants designated HV-1, HV-2, and HV-3 have been determined. Recently, Scharf et al., (1989) *FEBS Lett* 255:105 reported on ten additional hirudin sequences, strengthening the concept of hirudin as a "family of isoinhibitors."

Several laboratories have constructed synthetic genes for HV-1 and have expressed biologically active hirudin in microbial systems. These are reviewed in Johnson et al., (1989) *Seminars in Thrombosis and Hemostasis* 15(3):302. As shown in Table 1 therein, specific activities reported for purified recombinant hirudins show some variability, perhaps reflecting the degree of purity and/or differences in assay conditions. The naturally occurring protein is sulfated at tyrosine$_{63}$, although purified preparations may contain as much as 12% of the nonsulfated form (Chang (1983) *FEBS Lett* 164:307). Desulfation of the tyrosine results in a three- to ten-fold decrease in affinity for thrombin (see, Stone and Hofsteenage (1986) *Biochem* 25:4622; Dodt et al., (1988) *FEBS Lett* 229:87) indicating that sulfation of tyrosine$_{63}$ is responsible for the enhanced affinity of natural over recombinant hirudin.

Analogs of hirudin have also been produced by chemical modification or through recombinant DNA techniques. For example, European Patent Publication 273,800 discloses a hirudin analog having the putative native asparagine$_{47}$ substituted with lysine, arginine or histidine and the native tyrosine$_{63}$ substituted with glutamine or asparagine. As tested in a thrombin inhibition assay, the Arg$_{47}$ and Lys$_{47}$ variants of HV-2 are shown to be at least as active as native HV-2, while Glu$_{63}$ or His$_{47}$ variants are less active than the native form.

Degryse et al., (1989) *Protein Engineering* 2(6):459 similarly disclose that the Lys$_{47}$ and Arg$_{47}$ variants of HV-2 had lower (5- to 14-fold) dissociation constants than unmodified HV-2. (Actually, Lys$_{47}$ is the native residue at position 47 of HV-2; Lys$_{47}$ was designated an HV-2 variant due to a sequencing error.) Furthermore, the Lys$_{47}$ protein displayed enhanced antithrombotic activity in vivo, having a 100-fold lower ED$_{50}$ compared to HV-2 (Gln$_{47}$) in the rabbit Wessler venous thrombosis model. These results demonstrate that in vivo antithrombotic efficacy correlates with the dissociation (inhibition) constant which is an in vitro quantitative measure of the inhibition of thrombin by hirudin.

U.S. Pat. No. 4,668,662 discloses chemically synthesized HV-1 analogs having amino acid substitutions in either of the first two amino-terminal positions, as well as a modified Tyr$_{63}$. The hydroxyl position on the phenyl ring of Tyr63 may be a sulfate or a phosphate group. Hofsteenage et al., (1990) *Eur J Biochem* 188:55 incubated recombinant hirudin with [gamma-$^{32}$P] ATP and protein tyrosine kinase III to phosphorylate hirudin at Tyr$_{63}$. The inhibition constant of phosphatohirudin was 18 fM compared with 20 fM for that of sulphatohirudin.

U.S. Pat. No. 4,745,177 discloses desulfatohirudin and desulfatohirudin having the 2 carboxy-terminal residues removed. These proteins are produced by chemical or biological means to eliminate the sulfate ester from the hydroxyl group at Tyr$_{63}$.

U.S. Pat. No. 4,767,742 discloses hirudin shortened at the amino-terminus by up to two amino acids and at the carboxy-terminus by up to 17 amino acids, as well as the desulfated derivatives.

DISCLOSURE OF THE INVENTION

It has now been found that a class of chemically modified, amino acid substituted analogs of native hirudin, which have been prepared in accordance with the present invention, is capable of exhibiting the anticoagulant and antithrombotic activity of the native hirudin compounds.

The analog compounds of the present invention generally retain a core polypeptide sequence of amino acid residues which correspond in a defined way to the sequence AA$_4$–AA$_{62}$ of native hirudin, using the consensus sequence identified herein wherein the amino-terminal residue is valine. The present hirudin analogs result from modifications in the amino acid composition or modifications in the amino acid composition with secondary chemical treatment thereof, which retain both the chemical and physical stability, as well as the biological activity, of the native molecule.

The present invention is, therefore, in one aspect directed to analog peptide compounds having hirudin activity of the formula:

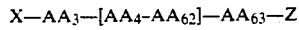

$$X-AA_3-[AA_4-AA_{62}]-AA_{63}-Z$$

wherein:

AA$_3$ is a conservative amino acid residue other than tyrosine that is not susceptible to electrophilic chemical modification;

AA$_4$–AA$_{62}$ represent amino acids 4 through 62 of native hirudin polypeptide;

AA$_{63}$ is a tyrosine residue or a tyrosine residue modified so as to contain an electron-withdrawing substituent in the 3- or 3-, 5- positions of the phenyl ring;

X is hydrogen or an N-terminal extension sequence corresponding to some or all of the native hirudin polypeptide sequence; and Z is a hydroxyl group or a C-terminal extension sequence corresponding to some or all of the native hirudin polypeptide sequence.

Also provided in accordance with aspects of the invention are pharmaceutical compositions for treating antithrombotic conditions, the compositions formulated so as to contain a hirudin analog polypeptide. The invention also encompasses a method of treating antithrombotic conditions and methods of making the novel hirudin analogs.

MODES OF CARRYING OUT THE INVENTION

Figure 1:
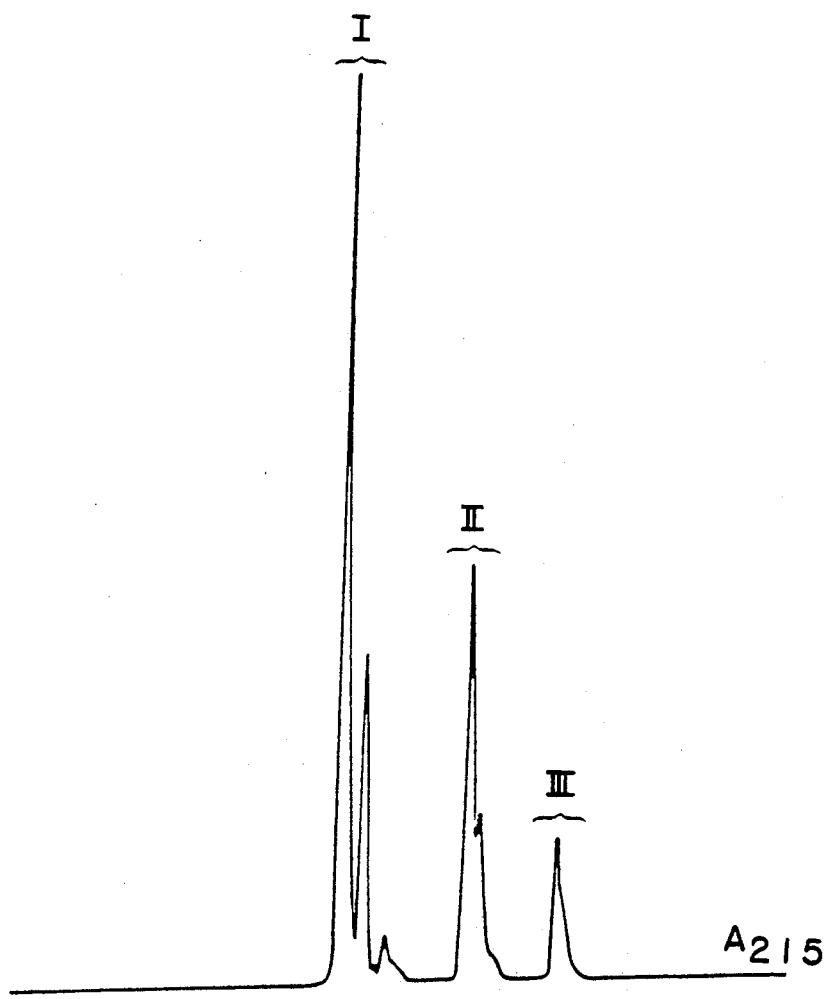
FIG. 1 shows RP-HPLC analysis of recombinant hirudin (r-hirudin) iodinated with a 0.8:1 molar ratio of NaI to r-hirudin.

In accordance with the present invention, novel hirudin analogs are provided which are capable of exhibiting anticoagulant and antithrombotic activity in mammals. Also included herein are methods of making these analogs as well as methods involving the pharmaceutical use of these hirudin analogs.

The practice of the present invention will employ, unless otherwise indicated, conventional techniques of molecular biology, microbiology and recombinant DNA techniques, and chemical modification of amino acids, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); a series, *Methods in Enzymology* (Academic Press, Inc.), and G. E. Means and R. E. Feeney, *Chemical Modification of Proteins*, Holden-Day, Inc., 1971. All patents, patent applications, and publications mentioned herein, both supra and infra, are hereby incorporated by reference.

As used herein, the term "hirudin" includes the entire hirudin family of isoinhibitors. The primary structures of three major hirudin variants, designated HV-1, HV-2, and HV-3, with a consensus sequence 1 (Con1) are set forth below. Consensus sequence 2 (Con2) illustrates additional variability from analysis of other hirudin variants (Scharf et al., (1989), supra). This sequence is also set forth below.

```
        10        20         30
HV-1 vvYTDCTESGQNLCLCEGSNVCG q GNKCILGSdGekNQ
     ||||||||||||||||||||||| ||||||||| || ||
HV-2 I TYTDCTESGQNLCLCEGSNVCGKGNKCILGSnGKgNQ
     |||||||||||||||||||||||||||||||| || ||
HV-3 I TYTDCTESGQNLCLCEGSNVCGKGNKCILGSqGKdNQ
```

-continued
```
Con1  itYTDCTESGQNLCLCEGSNVCGkGNKCILGS-Gk-NQ
Con2  It      i    ed      qd  d   (n)q    k
                                   (e)
```

```
         40        50        60
HV-1  CVTGEGTPkPqSHNdGDFEEIPEE_YLQ
      ||||||||  |||  ||||||||| |||
HV-2  CVTGEGTPnPeSHNnGDFEEIPEE_YLQ
      ||||||||  |||  ||||||||  |||
HV-3  CVTGEGTPkPqSHNqGDFEpIPE da.Yde

Con1  CVTGEGTPkPqSHN-GDFEeIPEe_Ylq
Con2                                 a
```

The lower case letters indicate positions of variability. For the consensus sequence Con1, lower case indicates a common position for two of the three variants HV-1, HV-2 or HV-3. For Con2, only positions of additional variability are provided. Positions denoted by a hyphen (—) or underscore (__) indicate more extensive variability or deletion, respectively.

The sequence of amino acid residues of the present analog compounds, including the core AA$_4$-AA$_{62}$ polypeptide, and preferred embodiments thereof, are defined in terms of amino acids of certain characteristics.

A "conservative" amino acid alteration is defined as one which does not produce a significantly adverse effect on the overall physical and/or biological properties of the molecule. The resulting effect of the analogs described herein may include both increased and decreased activity depending on the intended end use of the analog. For example, conservative amino acid substitutions for Tyr$_3$ (which is susceptible to undesirable electrophilic chemical modifications under conditions that result in a favorable modification of Tyr$_{63}$) are selected from the amino acids which are not susceptible to iodination or nitration but possess favorable steric and hydrophobic properties (i.e., properties similar to tyrosine). Preferred residues are phenylalanine, tryptophan, valine, leucine and isoleucine, more preferably phenylalanine and tryptophan.

Hirudin activity has been standardized as a function of thrombin activity, expressed in international NIH units. One antithrombin unit (ATU) of hirudin is the amount of hirudin that neutralizes 1 NIH unit of thrombin at 37° C., using fibrinogen as substrate. The anticoagulant activity of hirudin can be measured in a fibrin clotting assay which measures the kinetics of clot formation, using either human plasma or purified fibrinogen as the thrombin substrate. Hirudin activity is also defined by its ability to inhibit thrombin activity in a chromogenic substrate assay which measures the inhibition by hirudin of thrombin-catalyzed hydrolysis of small synthetic peptide substrates.

The hirudin analogs of the invention are intended to include polypeptides which are based on the amino acid sequences encoded by the known variants represented by the consensus sequence provided above, as modified at the tyrosine residues either by recombinant methods in which tyrosine is replaced by other amino acids and-/or by chemical treatment of the protein. These hirudin polypeptides are defined by the amino acid sequence:

$$X—AA_3—[AA_4-AA_{62}]—AA_{63}—Z$$

wherein:
  AA$_3$ is a conservative amino acid residue other than tyrosine that is not susceptible to electrophilic chemical modification;

AA$_4$–AA$_{62}$ represent amino acids 4 through 62 of the native consensus hirudin polypeptide;

AA$_{63}$ is a tyrosine residue or a tyrosine residue modifies so as to contain an electron-withdrawing substituent in the 3- or 3-, 5-positions of the phenyl ring;

X is hydrogen or an N-terminal extension sequence corresponding to some or all of the native hirudin polypeptide sequence; and Z is a hydroxyl group or a C-terminal extension sequence corresponding to some or all of the native hirudin polypeptide sequence.

Preferred embodiments of the hirudin polypeptides described above are those wherein X is Val-Val and Z is Leu-Gln, each group corresponding to the native N-terminal and C-terminal sequences of HV-1, respectively.

And as will be discussed below, preferred hirudin analogs within the aforementioned group are those wherein AA$_3$ is a non-tyrosine, conservative residue and is selected from the group of amino acid residues whose side chains are not susceptible to modification introducing electron-withdrawing substitutents. Such residues are generally classified as neutral, hydrophobic amino acids and include phenylalanine, tryptophan, valine, isoleucine, and leucine. Particularly preferred are phenylalanine and tryptophan. While not wishing to be bound by any theory, the inventors demonstrate herein that chemical modification, such as iodination or nitration, of the Tyr$_{63}$ in recombinant hirudin favorably enhances the inhibition of thrombin. The results suggest that the addition of electron-withdrawing substituents at the ortho position(s) relative to the hydroxyl group of the tyrosine ring causes a decrease in the pKa of the ring hydroxyl group resulting in the formation of a negative charge at neutral pH. This effect appears to mimic the negative charge of the sulfate group in native hirudin, resulting in an increased activity of recombinant hirudin. The inventors have also discovered that nitration of Tyr$_3$ in recombinant hirudin reduces thrombin inhibition activity. This effect can be eliminated by replacing Tyr$_3$ with phenylalanine, tryptophan, or another suitable amino acid capable of preventing chemical modification at amino acid position 3 of the hirudin molecule.

A secondary advantage of substituting tryptophan at amino acid position 3 is that tryptophan confers desirable fluorescent properties on hirudin.

The specificity of thrombin for binding macromolecular substrates appears to involve interactions at three distinct regions: (1) the basic specificity pocket in the active site region, which binds the side chains of lysine or arginine on the amino-terminal side of the scissile peptide bond; (2) the apolar-binding site, which binds proflavin, and (3) the anion-binding exosite, a region rich in basic amino acids that is important for the specific interaction of thrombin and fibrinogen. Each of these regions may involve hirudin binding.

In hirudin, modification of the acidic carboxy-terminal region of hirudin, either by deletion or substitution of residues (Dodt et al., (1987) supra, Braun et al., (1988) *Biochem* 27:6517) or by desulfation of Tyr$_{63}$ (Chang, (1983), supra), leads to an increase in Ki values. Common to all of these studies is an emphasis on the interaction of the carboxy-terminus of hirudin with thrombin. The present hirudin analogs present evidence that the amino-terminal region of hirudin also plays an important role in the specificity of hirudin-thrombin interaction.

Thus, in another embodiment of the invention, further modification of the amino-terminal segment of hirudin, containing residues 1-5, results in a major reduction in its affinity for thrombin. For example, simultaneous deletion of the amino-terminal Val and Tyr$_3$→Val, Thr$_4$→Gln and Asp$_5$→Ile substitutions result in a large reduction in thrombin inhibitory activity corresponding to greater than a $10^7$-fold increase in Ki and a $10^3$-fold increase in IC$_{50}$ using the chromogenic substrate, S-2238, and fibrinogen, respectively, as substrates. The large effect of these modifications on hirudin activity suggests that alterations of the amino-terminal segment can destabilize the interaction of other regions of hirudin with thrombin.

Production of the Protein

Compounds within the scope of the present invention can be synthesized chemically by means well known in the art such as, for example, solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups are suitable. For example, Boc-Gln-OH (i.e., a selected hirudin analog carboxy-terminal amino acid) can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart et al., *Solid-Phase Peptide Synthesis* (1969) W. H. Freeman Co., San Francisco, and Merrifield, (1963) *J Am Chem Soc* 85:2149-2154. These and other methods of peptide synthesis are also exemplified by U.S. Pat. Nos. 3,862,925, 3,842,067, 3,972,859, and 4,105,602.

The synthesis may be accomplished using manual techniques or automatically by employing, for example, an Applied BioSystems 430A Peptide Synthesizer (Foster City, CA) or a Biosearch SAM II automatic peptide synthesizer (Biosearch, Inc., San Rafael, CA), following the instructions provided by the manufacturer.

Alternatively, selected compounds of the present invention can be produced by expression of recombinant DNA constructs prepared in accordance with well-known methods. Such production is desirable to provide large quantities of the desired compound or alternative amino acid substituted embodiments of such compounds.

Most of the techniques which are used to construct vectors, transform cells, effect expression in transformed cells and the like are widely practiced in the art, and most practitioners are familiar with the standard resource materials which describe specific conditions and procedures. Illustrative methods as they apply to the peptides of the invention are set forth with particularity in U.S. Ser. No. 347,545, filed May 4, 1989, the teaching of which is incorporated herein by reference.

The nucleotide sequences encoding the hirudin analogs of the invention are available through the use of recombinant DNA methods or through use of synthetic chemical methods. As the amino acid sequence of hirudin is known, the appropriate nucleotide sequences can be synthesized using codons which are preferentially recognized by the specific host expression system to be used for protein production.

According to the method of the present invention, the nucleotide sequence may be altered to delete or substitute the codon specifying the tyrosine$_3$ residue with a codon specific for a residue whose side chain will not react with chemical agents capable of introducing electron-withdrawing substituents. In some instances, it may also be desirable to further alter the nucleotide sequence to create or remove restriction sites to, for example, allow insertion of the gene sequence into convenient expression vectors.

As an alternative to the preparation of synthetic oligonucleotides, it is also contemplated herein that desired nucleotide substitutions may also be performed using the polymerase chain reaction (PCR) technique as disclosed in U.S. Pat. Nos. 4,683,202 and 4,683,195. In its simplest form, PCR is an in vitro method for the enzymatic synthesis of specific DNA sequences, using two oligonucleotide primers that hybridize to opposite strands and flank the region of interest in the target DNA. A repetitive series of steps involving template denaturation, primer annealing, and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., (1985) *Science* 230:1350.

The hirudin analog may be produced either as a mature protein or as a fusion protein, or may be produced along with a signal sequence in cells capable of processing this sequence for secretion. An example of a vector system capable of expressing the hirudin analogs as a fusion protein employs pNP6, a pBR322 derivative vector comprising the colicin E1 expression control sequence. This vector is described in U.S. Pat. No. 4,897,348, the relevant parts of which are specifically incorporated herein by reference. U.S. Ser. No. 347,545, supra, describes an improved pNP6 derivative, pBR6-CRM/CTAP, having changes in the colicin E1 promoter region; unique restriction sites for the insertion of the desired gene sequence; the catabolite repressor protein binding site deleted, thereby facilitating bacterial cell growth in the presence of glucose; and a leader peptide comprising the connective tissue-activating peptide-III (CTAP-III). The specific portions of this application relating to the construction of this vector are also incorporated herein by reference.

Expression may be achieved in a variety of host systems including. in particular, bacterial systems, as well as mammalian and yeast-based systems. In addition, other cell systems have become available in the art, such as the baculovirus vectors used to express protein-encoding genes in insect cells. The expression systems used in the present invention are merely illustrative, and it is understood by those in the art that a variety of expression systems can be used.

Chemical Modification

The chemical modification of the hirudin analogs of the present invention may employ a number of methods for introducing different electronegative substituents on the ring of tyrosine$_{63}$. Apparently, the introduction of such substituents on the ring in the ortho position(s) relative to the hydroxyl enhances thrombin binding by lowering the pKa of the ring hydroxyl.

Chemical modification, as provided herein, can be accomplished using halogenating agents, such as, for example, iodine, fluorine, chlorine; nitrates, such as, for example, tetranitromethane; sulfates ($SO_4^{-2}$); phosphates ($PO_4^{-2}$) and carbonates ($CO_3^{-2}$). Generally, the reactions are run at neutral pH, more specifically, at a pH ranging from about 6.5 to about 8.5. Depending upon the specific chemical agent used to modify Tyr$_{63}$, the molar ratio of the chemical agent to hirudin ranges from about 0.020:1 to about 250:1.

Also contemplated by the present invention are hirudin analogs wherein further chemical modification of the primary amino acid sequence includes conjugation with saccharides, polyethylene glycols (PEGs), and polyoxethylene glycols (POGs) as shown in U.S. Pat. Nos. 4,179,337 and 4,847,325. If PEGylation is desired, additional amino acid substitutions or expression as a fusion protein are suggested, in view of the PEG's specificity to lysine and N-terminal residues. Substitution of the Lys$_{47}$ residue with, for example, Arg, would prevent any unfavorable PEGylation of hirudin at position 47.

Assays for Hirudin Activity

There are a number of activity assays developed to determine the quality of hirudin preparations and for use in quantitating hirudin in various biochemical and pharmacological experiments. Two of these methods set forth below may be used routinely and reproducibly. The first, a chromogenic substrate assay, measures the inhibition by hirudin of thrombin's ability to hydrolyze small synthetic peptide substrates. The second, a fibrin-clotting assay, measures the kinetics of clot formation, using either human plasma or purified fibrinogen as the thrombin substrate.

In the chromogenic assay, antithrombin activity is detected by measuring the inhibition of release of p-nitroaniline from, e.g., the chromogenic substrate H-D-phenylalanyl-L-pipecolyl-L-arginine-p-nitroanilide dihydrochloride (S-2238, supplied by Kabi Vitrum) by thrombin in the presence of hirudin. Thrombin concentration is 2 nM (typically 0.12 NIH units/ml), and hirudin can be assayed reproducibly at an approximate concentration range of 0.3 to 1 nM, using 296 uM substrate in 50 mM Tris buffer, 100 mM NaCl, pH 7.8, and 0.1% polyethylene glycol-6000 (PEG). PEG is included to inhibit binding of thrombin to the plastic surface of the microplate or cuvette; for the same reason, reaction vessels are pretreated with 1% PEG-20,000 prior to assay.

Hirudin inhibits the thrombin-mediated conversion of fibrinogen into a fibrin clot. This anticoagulation activity can be assayed by monitoring clot formation when purified human fibrinogen (5 mg/ml, final concentration) is mixed with human alpha-thrombin (0.06 NIH units/ml, final concentration) and varying hirudin concentrations in 50 mM Tris, 100 mM NaCl, 0.25% PEG-6000, pH 7.4. The hirudin concentration at 50% inhibition is then calculated from the titration curve.

For the clotting assay, hirudin is diluted to 50 ul in assay buffer (50 mM Tris-HCl, 120 mM NaCl, 0.5% PEG-6000, pH 7.4), added to 50 ul of human alpha-thrombin (0.2 pmole) in assay buffer containing 40 mM calcium chloride (final thrombin concentration equal to 1 nM), and incubated for 5 min in a 96-well microtiter plate at room temperature. The reaction is initiated by addition of 100 ul of fibrinogen (10 mg/ml) in assay buffer (without PEG) and the solution mixed for 10 sec. The turbidity of the reaction mixture is monitored at 405 nm using, for example, the Vmax Kinetic Microplate Reader (Molecular Devices Corporation). Data acquisition and processing may be accomplished by a microcomputer interfaced to the microtiter plate reader using software provided by Molecular Devices Corporation.

The $IC_{50}$ is determined from the linear least squares fit of the data and calculated as the hirudin concentration at which the initial velocity of the thrombin reaction is inhibited by 50%.

Administration and Use

Compounds of the present invention are shown to have anticoagulant and antithrombotic activity in in vitro models which simulate in vivo mammalian conditions. Thus, these compounds, and compositions containing them, can find use as therapeutic agents in the treatment of various antithrombotic conditions such as, for example, venous and arterial thrombosis, particularly as an adjunct to fibrinolytic therapy, disseminated intravascular coagulation, antithrombin-III deficiency, to inhibit excessive fibrin formation during wound healing, and as an agent for the treatment of some forms of metastatic cancer.

Thus, the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered for clinical use in humans and other mammals in a manner similar to other therapeutic agents. In general, the dosage required for therapeutic efficacy will range from about 0.01 to 100 mg/kg, more usually 0.1 to 20 mg/kg of the host body weight. Alternatively, dosages within these ranges can be administered by constant infusion over an extended period of time until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. While liquid solutions of the hirudin analogs may be used directly on or under wound dressings, reconstituted compositions are useful for salves, gel formulations, foams and the like for wound healing. Additional formulations which are suitable for other modes of administration include suppositories, intranasal pulmonary aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%-2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%-95% of active ingredient, preferably 25%-70%.

The peptide compounds may be formulated into the compositions as neutral or salt forms. Pharmaceutically acceptable nontoxic salts include the acid addition salts (formed with the free amino groups) which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display antithrombotic activity, compounds of the present invention can also be employed as intermediates in the synthesis of such useful compounds.

The following examples further illustrate the various embodiments of the invention. These examples are not intended to limit the invention in any manner.

EXAMPLES

Example 1

Iodination of Recombinant Hirudin

Recombinant hirudin (HV-1) was produced from a synthetic gene using an E. coli expression system derived from the colicin E1 operon (U.S. Pat. No. 4,897,348). An expression cassette, described in co-pending U.S. Ser. No. 07/347,371, filed May 4, 1989, was constructed consisting of a 472 basepair synthetic DNA containing the optimally designed structural gene and the colicin E1 regulatory sequences. The protein was purified to homogeneity by anion exchange chromatography and reverse-phase high pressure liquid chromatography (RP-HPLC).

Recombinant hirudin was iodinated with varying levels of NaI ranging from 0.027:1 to 23:1 (moles NaI:moles r-hirudin). The reaction was performed at pH 7.2 in a total volume of 0.2 ml containing 0.05 ml Enzymobeads (BioRad), 1.92 to 1670 uM NaI, 71.4 uM r-hirudin, and 50 mM sodium phosphate. The reaction was initiated by addition of 0.25% alpha-D-glucose (which had been mutarotated overnight) and terminated after 20 to 40 min at room temperature by centrifugation to remove Enzymobeads from suspension. The iodination products were separated from unreacted material by HPLC on a reverse-phase C-4 column (Vydac 214TP54). Elution was performed in 0.065% (v/v) trifluoroacetic acid (TFA) with an ascending linear gradient of 15 to 30% acetonitrile at a rate of 0.5% acetonitrile per min. Absorbance was monitored at 215 nm.

At a molar ratio of 0.08:1 (NaI:r-hirudin), two products were detected by HPLC in addition to the starting material. The total mass of the two iodinated products, which were in roughly equal proportion to one another, were judged by inspection to be approximately 5% (by mass) of the starting material. When the molar ratio was reduced 3-fold to 0.027:1, both products were just barely detectable. This result implied that iodination of r-hirudin under these conditions inevitably results in two products.

When the NaI:r-hirudin ratio was increased 3.33-fold to 0.27:1, additional iodination products were formed as evidenced by the appearance of new HPLC peaks. A further increase in the molar ratio of NaI:r-hirudin resulted in yet additional peaks detectable by HPLC, as shown in FIG. 1. There are three sets of peaks: the left-most set (designated pool I) contains unreacted r-hirudin (at the far left) and two additional peaks. The middle set of peaks (designated pool II) contains three peaks which are poorly resolved. The material at the right (designated pool III) appears to contain a single reaction product; however, a higher level of iodine substitution resulted in three peaks eluting at this position.

Next, the influence of iodination on r-hirudin specific activity and on its inhibition constant (Ki) for human alpha-thrombin (that is, the dissociation constant of the hirudin-thrombin complex) was examined. In order to produce a sufficient quantity of iodinated protein, the reaction was run at a ratio of 0.80:1 (NaI:r-hirudin). The three major groups of peaks shown in FIG. 1 were pooled, and the HPLC solvent was removed by lyophilization. Specific activities of the pooled iodinated products were then determined from the analysis of hirudin-thrombin titration curves compared to the unreacted material.

For the majority of the experiments described herein a concentrated stock of human alpha-thrombin was diluted to 1 uM in 5 mM Tris buffer, 0.5 M NaCl, pH 6 and stored at −60° C. over a period of several months. Aliquots were thawed and diluted to 1 nM before assay.

Specific activity of the r-hirudin standard was repeatedly measured at 37° C. over a seven month period using a recording spectrophotometer. Conditions were the same as described above except that reactions were performed in polystyrene cuvettes. The rate of change at 405 nm was converted to antithrombin units (ATU) using the relation 1 ATU/ml = 1.25 Abs unit/min decline (KabiVitrum technical data). Protein concentration was determined by amino acid composition analysis. The mean specific activity by this method was 10.2 ATU/ug, s.d. 0.83, range = 9.04 to 11.5, for eight independent determinations.

Activities and inhibition constants for the various iodination products are given in Table 1. While specific activities were relatively unaffected by iodination, binding constants varied over nearly an order of magnitude. (It should be noted that specific activity is a less sensitive indication of inhibition potency than is the inhibition constant, Ki). Thus, r-hirudin from pool II and pool III bound, respectively, 2-fold and 8-fold more tightly to thrombin in comparison to the unreacted material. The Ki of r-hirudin from pool I was intermediate between unreacted r-hirudin and pool II. This is consistent with the presence of unreacted material in pool I (i.e., the leftmost peak of pool I in FIG. 1).

EXAMPLE 2

Nitration of Recombinant Hirudin

A 63.5 uM solution of r-hirudin was nitrated by addition of 12.7 mM tetranitromethane (purchased from Aldrich Chemical Co.; 200:1 molar ratio of TNM:hirudin) in 50 mM Tris, pH 8 in a volume of 45 ul. After 1 hour with constant shaking, the reaction was terminated by lowering the pH to 2 by addition of 955 ul of 0.065% TFA in 15% acetonitrile. Reaction products were separated from unreacted material by HPLC on a reverse phase C-4 column. The chromatogram was developed in 0.065% TFA with an ascending linear gradient of 15 to 30% acetonitrile at a rate of 0.25% acetonitrile per minute. UV-absorbing peaks were monitored at 215 nm (to measure protein) and 360 nm (the absorbance maximum of 3-nitro-tyrosine under acidic conditions).

Tight-binding Inhibition Analysis

Inhibition constants (Ki) were determined in steady-state velocity experiments using the synthetic substrate S-2238 (Kabi Vitrum). Reactions were carried out at room temperature in plastic microtiter plates at a concentration of 200 uM substrate in 50 mM Tris, 100 mM NaCl, 0.1% PEG-6000 at pH 7.8; reactions were initiated by addition of thrombin to 0.2 nM. Hirudin was varied over a range that included four concentrations above and four below the concentration of thrombin with a minimum of three determinations at each hirudin concentration. Reaction velocities were measured from the change in optical density at 405 nm using a Vmax Kinetic Microplate Reader and software by Molecular Devices Corporation (Menlo Park, CA). Release of the chromophore was monitored at 405 nm.

Steady-state velocities were fitted to the rate equation of Morrison [(1969) *Biochem Biophys Acta* 185:269] for tight-binding inhibition kinetics. When steady-state velocities are plotted as a function of hirudin concentration, the resulting curve is described by the equation $$2*T*Vi/Vo = ([(Ki' + X*H - T)^2 + 4*Ki'*T]^{0.5} - Ki' - X*H + T)$$

where H = hirudin concentration, T = thrombin concentration, Vi and Vo are initial rates of the inhibited and uninhibited reactions, respectively, X is a factor that converts hirudin concentration into units of molarity, and $Ki = Ki'/(1+[Substrate]/Km)$ for competitive inhibition. The Km was taken to be 3.63 uM as determined by Stone and Hofsteenage [(1986) *Biochem* 25:4622] under similar conditions. The data was fitted to the equation by nonlinear, least-squares regression analysis, yielding estimates of x, Vo and Ki'.

Slow Tight-binding Inhibition Analysis

By increasing the ionic strength, the rate of interaction between hirudin and thrombin can be inhibited TABLE 1
Specific Activities and Inhibition Constants for Iodination Products of r-Hirudin

| r-Hirudin | Total Activity (Antithrombin Units) | Total Mass (ug) | Specific Activity (ATU/ug) | Ki(fM) |
|---|---|---|---|---|
| Unreacted | 347 | 40.0 | 8.68 | 296 |
| Iodinated Pool I | 199 | 28.9 | 6.89 | 231 |
| Iodinated Pool II | 96.3 | 11.4 | 8.45 | 139 |
| Iodinated Pool III | 19.6 | 3.23 | 6.08 | 36.9 | sufficiently that the steady-state velocity is attained slowly. Under this condition, the progress curve of formation of the enzyme-inhibitor complex is described by the following set of equations (Morrison and Stone, (1985), Comments Mol Cell Biophys 2:347):

$$P = Vf*t + [(1 - g)(Vi - Vf)/(k*g)]*\ln[(1 - g*e^{[-k*t]})/(1 - g)]$$

$$g = (Ki' + H + T - Q)/(Ki' + H + T + Q)$$

$$Q = [(Ki' + T + H)^2 - 4*T*H]^{0.5}$$

$$Vf = Vi*(T - H - Ki' + Q)/(2*T)$$

where t=time, Vi is the initial reaction rate and Vf is the final steady state rate, k=k1'*Q and k1' is the apparent association rate constant. Nonlinear regression analysis yields estimates of Ki' and k1; the apparent dissociation rate constant, k2', is the product of Ki' and k1'.

Slow tight-binding experiments were performed identically to tight-binding studies, except that the NaCl concentration was raised to 0.5M and the hirudin:thrombin ratio was varied from 0.5:1 to 6:1 or, in the case of r-hirudin nitrated at Tyr3 which had relatively weak thrombin binding, from 1:1 to 12:1. Computer software was used to acquire progress curves and smooth them using a cubic spline technique and for nonlinear regression analysis of both tight-binding and slow tight-binding data.

Figure 2:
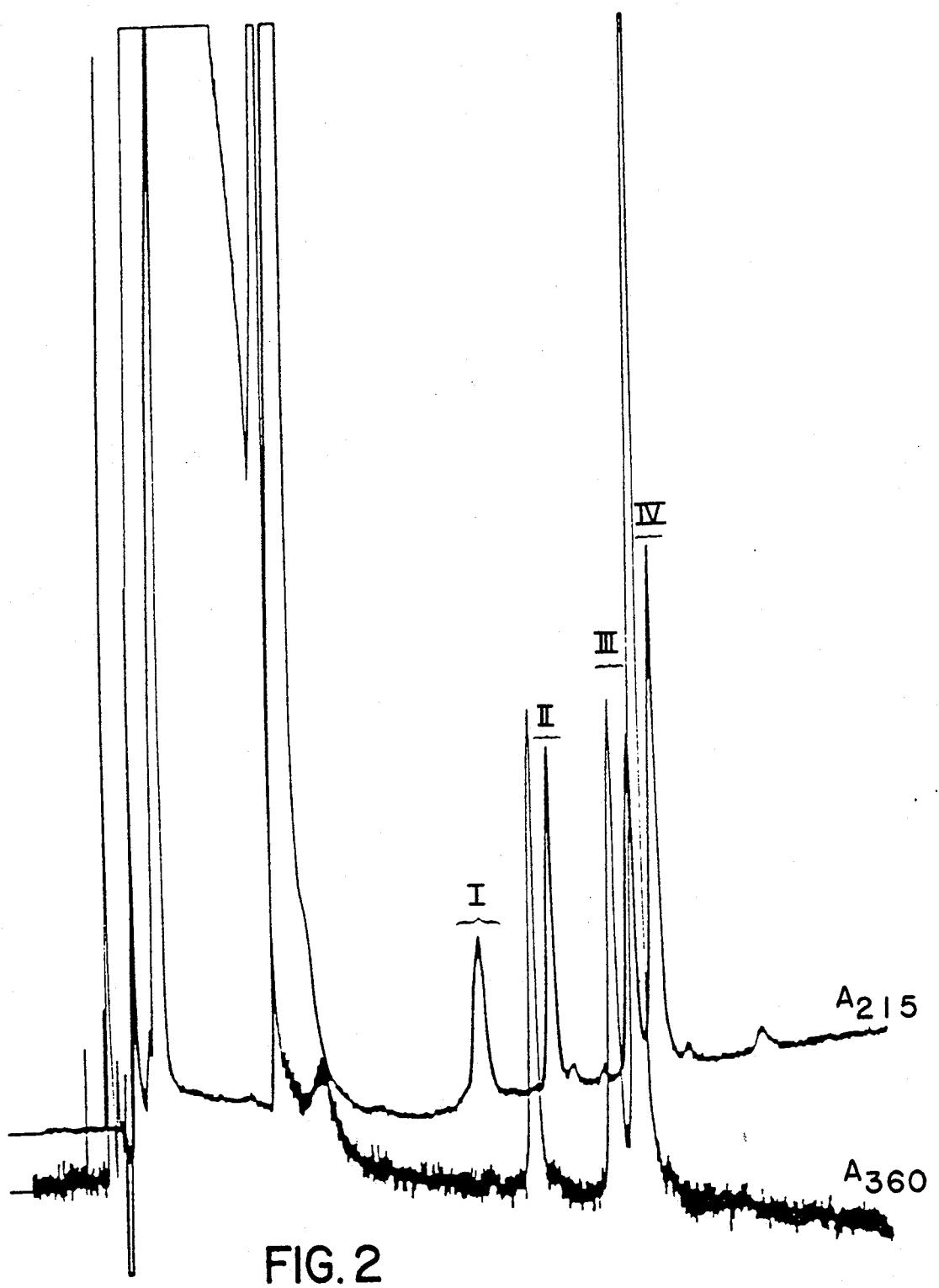
FIG. 2 shows RP-HPLC analysis of r-hirudin after tetranitromethane (TNM) treatment using a 200:1 molar ratio of TNM:hirudin at pH 8.

Nitration of r-hirudin under these conditions resulted in six main peaks detectable by reverse-phase HPLC as shown in FIG. 2. Control reactions lacking protein indicated that the two early peaks (at the far left) were from tetranitromethane. Peak I is unreacted r-hirudin based on its retention time and the absence of absorbance at 360 nm (specific for nitro-tyrosine).

Because tetranitromethane reacts specifically with tyrosine residues in proteins, the altered retention time and the presence of absorbance at 360 nm for peaks II through IV suggests that these peaks represent the three possible 3-nitro derivatives that can arise from a protein containing two tyrosine residues. By comparing the relative peak heights at 360 and 215 nm for each of the peaks II, III and IV it is apparent that the 360:215 ratio is roughly twice as high for peak IV as for peaks II or III. We conclude from this data that peak IV is hirudin nitrated at both Tyr3 and Tyr63. Peaks II and III must therefore represent the two possible mono-nitrated products.

Figure 3:
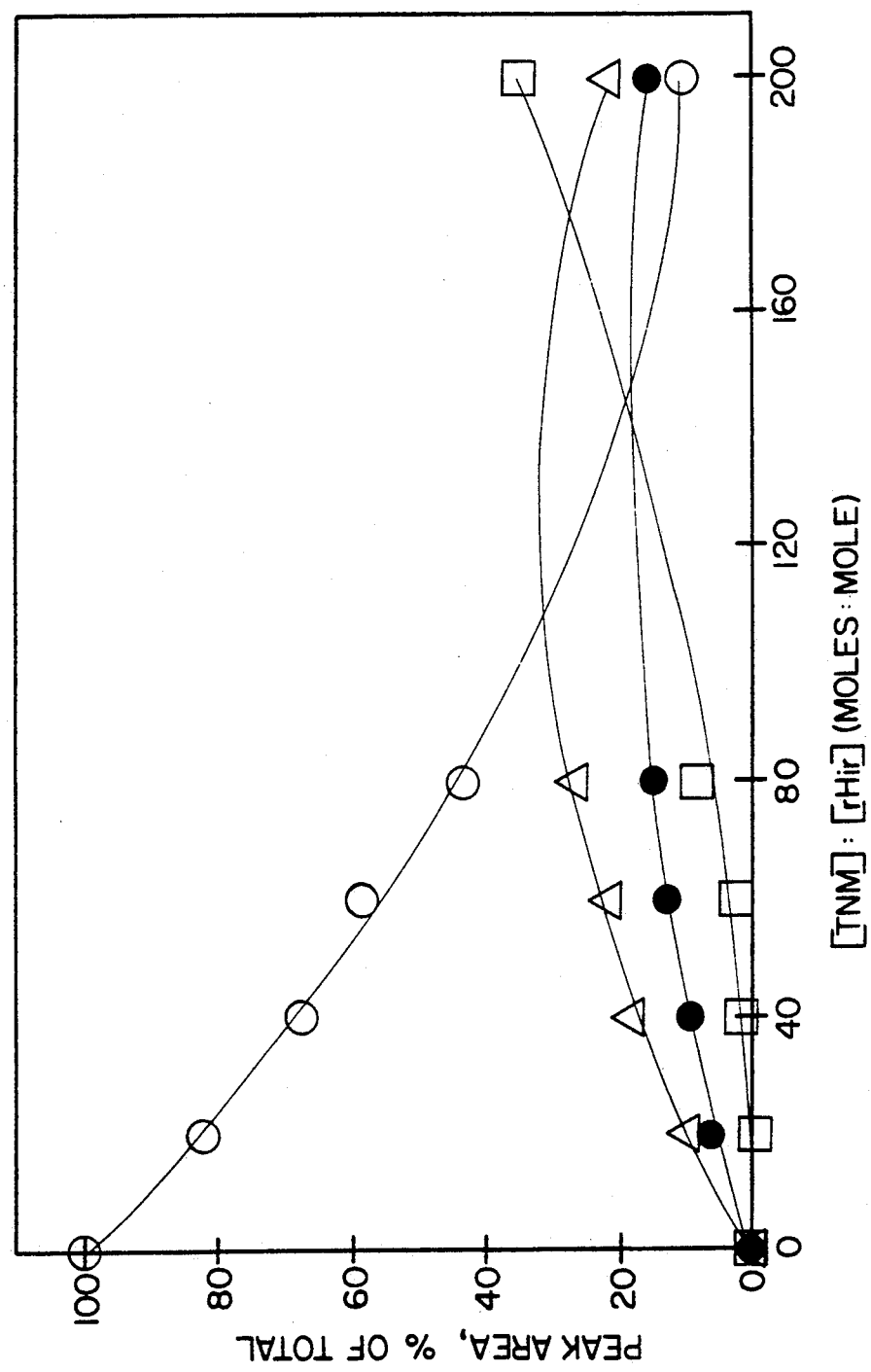
FIG. 3 is an illustration showing the kinetics of product formation assessed by plotting peak area as a function of TNM concentration at a fixed level of r-hirudin. Peak I [unmodified r-hirudin], open circles; Peak II [r-hirudin (nitro-Tyr$_3$)], closed circles; Peak III [r-hirudin (nitro-Tyr$_{63}$)], triangles; and Peak IV [r-hirudin (dinitro Tyr$_3$, Tyr$_{63}$)], squares.
Figure 4A:
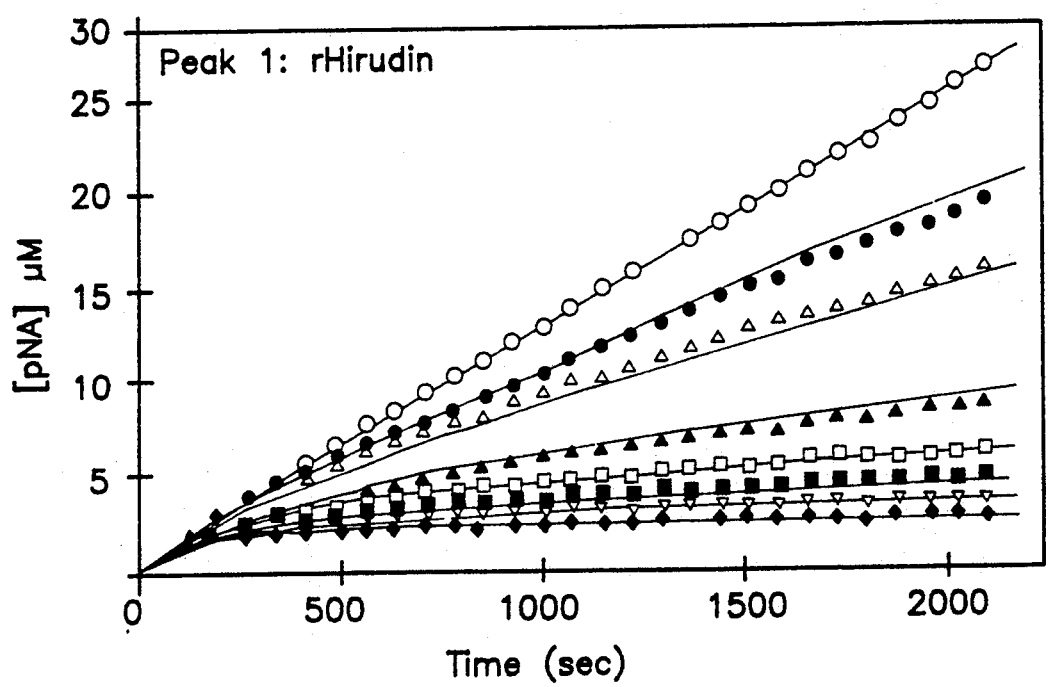
FIG. 4 shows slow-binding inhibition of thrombin by nitrated r-hirudin. Hirudin concentrations are as follows, 0 (open circles); 50 pM (closed circles); 100 pM (open triangles); 200 pM (closed triangles); 300 pM (open squares); 400 pM (closed squares); 500 pM (open inverted triangles); 600 pM (closed inverted triangles); 800 pM (open diamonds); and 1000 pM (closed diamonds).
Figure 4C:
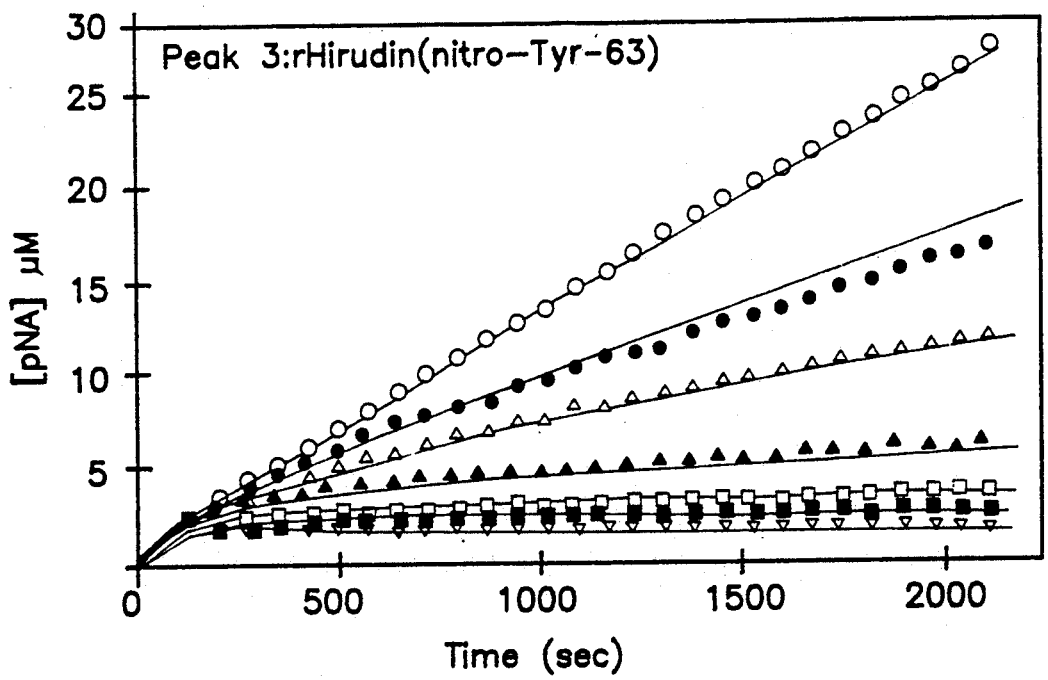
Figure 4B:
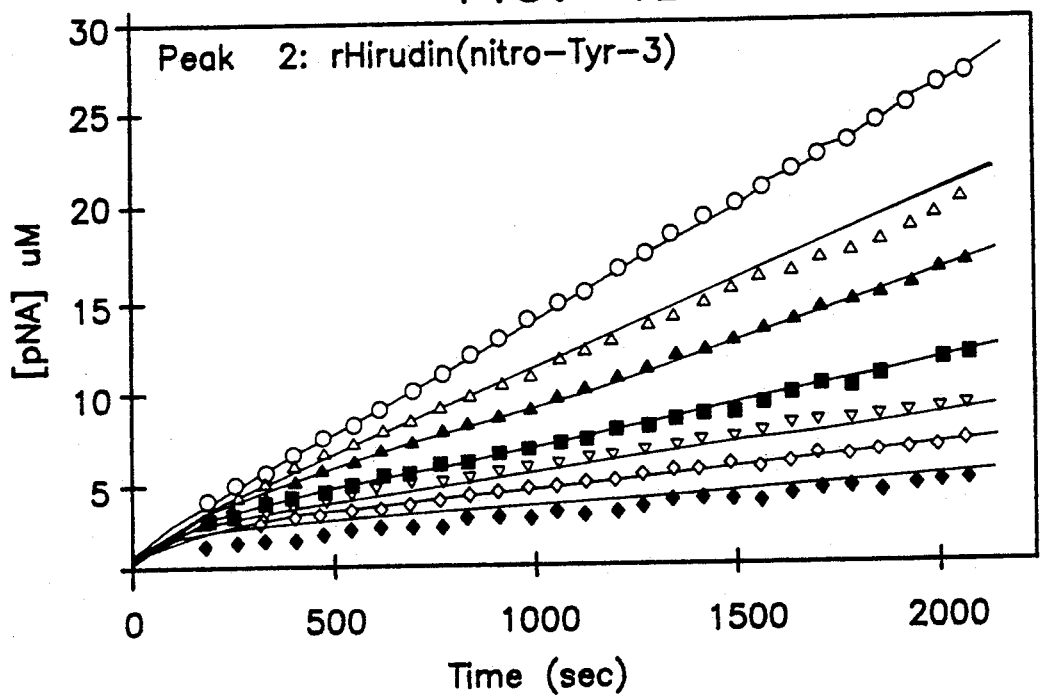
Figure 4D:
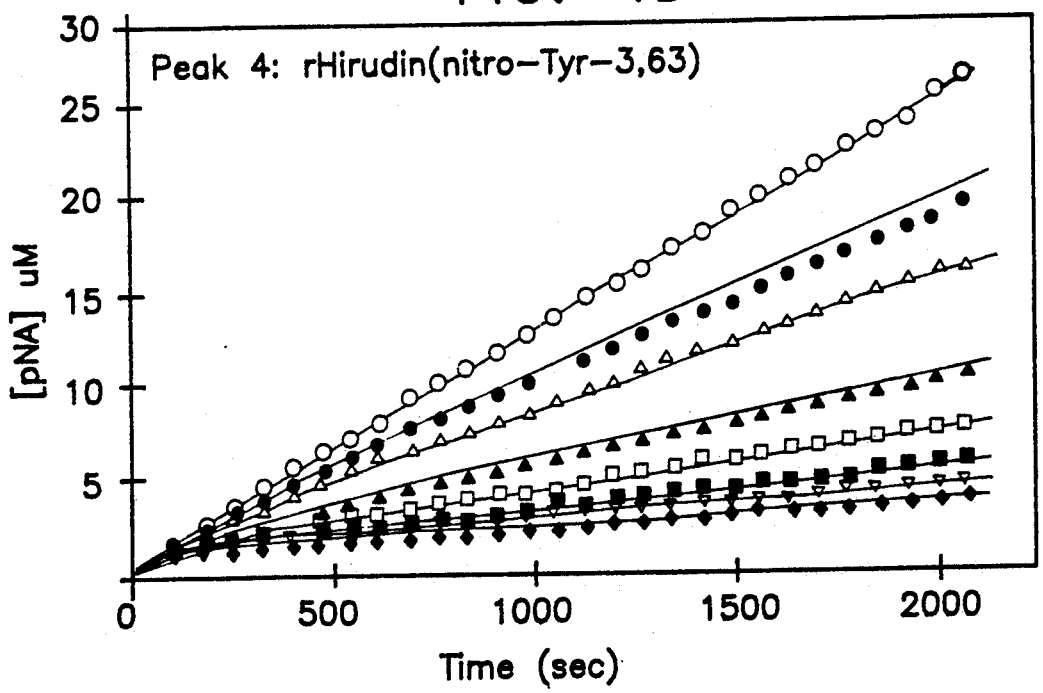

The kinetics of product formation was assessed by plotting peak area as a function of TNM concentration at a fixed level of r-hirudin (FIG. 3). As shown therein, production of peaks II and III are about parallel throughout the range of TNM concentrations tested and exceed peak IV production up to the highest level of TNM tested (200:1 TNM:r-hirudin), at which point peak IV becomes the predominant product. These results suggest that production of peak IV is dependent on prior formation of either or both peaks II and III. Therefore, evidence from both reaction kinetics and the ratios of absorbance at 360:215 nm indicate that peaks II and III are mono-nitrated forms of r-hirudin and that peak IV is nitrated on both tyrosine residues. Furthermore, these results indicate the difficulty of selective modification of either tyrosine since they exhibit similar reaction kinetics.

Amino acid analyses were determined using a Beckman 6300 amino acid analyzer following hydrolysis in HCl for 24 hr. Amino acid compositions for modified and unmodified r-hirudin were in agreement with values determined from the nucleotide sequence of the synthetic genes.

The first 15 residues of the N-terminal sequence of chemically modified and unmodified r-hirudin samples were determined using an Applied Biosystems 470A gas-phase protein sequenator with separation on a Brownlee C18 column (2.1 mm×22 cm) at 52° C. in 110 mM sodium acetate pH 3.9, 5% tetrahydrofuran (buffer A) to acetonitrile (buffer B), 10 to 37% buffer B linear gradient over 19 minutes.

N-terminal sequence analysis of nitrated r-hirudin demonstrated that peaks II and IV contain 3-nitro-tyrosine at position 3, while Tyr3 of peak III is unmodified; amino acid composition analysis confirmed that tyrosine in peaks II and III were 45% and 47% nitrated, respectively, while peak IV contained 100% 3-nitro-tyrosine.

After lyophilization to remove HPLC solvents, thrombin inhibition analysis was carried out for each of the peaks I through IV. Table 2 compares inhibition constants for the different nitrated forms of r-hirudin at physiologic ionic strength (I)=0.125, and at I=0.525.

TABLE 2

Influence of r-Hirudin Nitration on the Inhibition Constant (Ki) for Human alpha-Thrombin at Low and High Ionic Strength.

| r-hirudin Modification | Ki (pM) [Relative to Peak I][a] | |  | |
|---|---|---|---|---|
|  | At 0.125 I | | At 0.525 I | |
| None | 0.27 | [100] | 1.1 | [100] |
| nitro-Tyr3 | 2.7 | [1000] | 6.8 | [600] |
| nitro-Tyr63 | 0.082 | [31] | 0.45 | [41] |
| nitro-Tyr3-Tyr63 | 0.39 | [140] | 3.1 | [230] |

[a]Assays were performed at 200 uM S-2238 in 50 mM Tris, 0.1% PEG 6000, pH 7.8, and initiated with 200 pM thrombin. Data at 0.125 I was analyzed as described under Tight-binding Inhibition Analysis and at 0.525 I as described under Slow Tight-binding Inhibition Analysis.

As expected, high I weakens the binding of all modified forms of r-hirudin to thrombin. r-Hirudin (nitro-Tyr63) binds thrombin more tightly than non-nitrated r-hirudin, whereas binding of r-hirudin (nitro-Tyr3) to thrombin is reduced.

FIG. 4 shows the reaction progress curves for the slow-binding inhibition analysis of nitrated-r-hirudin. Table 3 summarizes the apparent association and dissociation rate constants (k1', k-1') calculated from the progress curves determined at high I. The reduction in Ki for r-hirudin (nitro-Tyr63) is almost entirely attributable to the 2.3-fold increase in k1'; the dissociation rate constant (k-1') was largely unaffected by nitration at this position. For r-hirudin (nitro-Tyr3) the major cause of the large increase in Ki compared to unmodified r-hirudin is the 5-fold increase in k-1', combined with a slight reduction in k1.

TABLE 3

Influence of Nitration on Apparent Inhibition Parameters of R-hirudin for Human alpha-Thrombin Determined at I = 0.525

| r-hirudin Modification | Binding and Rate Constants [% Relative to Unmodified][a] | | | | | |
|---|---|---|---|---|---|---|
|  | Ki' (pM) | | k1' (uM$^{-1}$s$^{-1}$) | | k-1' (s$^{-1}$ × 10$^6$) | |
| None | 74 | [100] | 6.1 | [100] | 450 | [100] |
| nitro-Tyr3 | 440 | [590] | 4.9 | [81] | 2180 | [480] |
| nitro-Tyr63 | 36 | [48] | 14 | [230] | 500 | [110] |
| dinitro-Tyr3, | 170 | [230] | 11 | [180] | 1900 | [410] |

TABLE 3-continued

Influence of Nitration on Apparent Inhibition Parameters of R-hirudin for Human alpha-Thrombin Determined at I = 0.525

Binding and Rate Constants [% Relative to Unmodified][a]

| r-hirudin Modification | Ki' (pM) | k1' (uM$^{-1}$ s$^{-1}$) | k-1' (s$^{-1}$ × 10$^6$) |
|---|---|---|---|
| Tyr$_{63}$ | | | |

[a]Assays were performed at 0.525 I as described in Table 2 and analyzed as described in Slow Tight-binding Inhibition Analysis.

Recombinant hirudin (dinitro-Tyr$_3$, Tyr$_{63}$) behaves as a hybrid between the two singly substituted r-hirudin analogs with respect to changes in k1' and k-1'. The increase in its association rate due to nitration at Tyr$_{63}$ is apparently offset by the modification at Tyr$_3$. In contrast, k-1' for r-hirudin (dinitro-Tyr$_3$, Tyr$_{63}$ is about the same as for r-hirudin (nitro-Tyr$_3$) which is consistent with the absence of an effect on k-1' for r-hirudin modified at Tyr$_{63}$.

EXAMPLE 3

Construction of Recombinant Hirudin Mutants

A synthetic gene encoding the native hirudin polypeptide was constructed using the pBR-CRM-CTAP expression vector system in which r-hirudin is produced as a fusion protein (connected by a single methionine residue) with connective tissue-activating peptide III (CTAP-III), a protein with unusually high stability in *E. coli* that stabilizes hirudin in vivo. The construction of this vector is disclosed in U.S. Ser. No. 347,545, supra.

Hirudin mutants were constructed by mutagenesis of the synthetic gene for hirudin variant 1 (HV-1) using the polymerase chain reaction, with a 5'-sense mutagenic primer (38- or 35-bases) containing the changes(s) specifying the amino acid substitution(s) desired, and a common 20-base anti-sense primer, as shown below.

common 20 base 3'-primer:
 5' ACCATCCGGGCACGGCATAC 3' mutagenic 38-base 5'-primer:
 5' ACAGAATTCTCGTTAACATGGTTGTA<u>TTC</u>ACTGATTGC 3' Phe
 5' ACAGAATTCTCGTTAACATGGTTGTA<u>TGG</u>ACTGATTGC 3' Trp
 5' ACAGAATTCTCGTTAACATGGTTGTA<u>ACT</u>ACTGATTGC 3' Thr mutagenic 35-base 5'-primer:
 5' ACAGAATTCTCGTTAACATGGTTGTA<u>CAG</u>ATTTGC 3' VVQI The PCR-amplified sequence was digested with EcoRI, purified by gel electrophoresis, and used to replace the wild-type sequence in the plasmid. *E. coli* MM294 cells were transformed with the recombinant plasmid and clones were screened by restriction analysis for the proper orientation of the EcoRI insert. The proper DNA sequence was confirmed by double-stranded DNA sequencing.

Cells containing the hirudin expression plasmid were grown in a fermenter (or, alternatively, in shake flasks) at 37° C. in media containing 50 ug/ml ampicillin. Upon reaching an optical density of 4 (for fermenter cultures), protein expression was induced with mitomycin C (1 mg/L) for 4 hours. Cells were harvested by centrifugation and resuspended and lysed in 0.1 culture volume of 6M guanidine-HCl (Gnd-HCl), 50 mM Tris-HCl (pH 7.5), 1 mM EDTA, at 5°-10° C. in a Stansted Cell Disrupter at an operating pressure of 11-12,000 PSI and a flow rate of 150-200 ml per minute. Cellular debris was removed by centrifugation.

The supernatant solution containing the fusion protein was adjusted to 0.2M phosphoric acid and 2.5 mM sodium thiosulfate (to protect free sulfhydryl groups from chemical modification by cyanogen bromide [CNBr]). The solution was purged of oxygen with argon and CNBr was added to a final concentration of between 0.1 and 0.4M. The reaction was incubated for 6 to 20 hours in the dark at room temperature. Progress was monitored by analytical reverse phase HPLC (RP-HPLC; described below). The reaction typically proceeded to greater than 90% completion, at which time the solution was dialyzed extensively to remove excess sodium thiosulfate (which interferes with subsequent sulfhydryl reduction), and freeze dried to remove residual CNBr. The yield of hirudin after the CNBr cleavage step was 50-100 mg per liter of original culture grown under medium density fermentation conditions.

Quantitation of hirudin was determined by thrombin inhibitory activity using the chromogenic substrate assay in comparison to a hirudin standard whose concentration was determined by amino acid composition analysis on a Beckman 6300 amino acid analyzer (using internal amino acid standards of known concentration). Approximate calculation of the amount of hirudin in a sample where determination of activity is impractical (for example, a CNBr cleavage reaction) was made by comparison of the integrated sample peak area and the hirudin standard peak area on an analytical RP-HPLC column (Vydac 214TP54, 25×0.46cm, 300 angstroms). The column was developed using 0.065% trifluoroacetic acid (TFA) with an ascending linear gradient of 15 to 30% acetonitrile at a rate of 0.5% per minute and a flow rate of 2 ml/minute. Oxidized and reduced hirudin elute at characteristic positions identical with purified hirudin having specific activity values greater than 10 antithrombin units per ug.

In preparation for RP-HPLC purification, the freeze dried crude powder from the CNBr reaction was dissolved in 50 ml (per liter of fermentation culture) of 2 M Gnd-HCl, 0.1M Tris (to pH 9-10) (or, alternatively, 0.1M NaHCO$_3$ to pH 9-10), 1 mM EDTA, 0.1M dithiothreitol (DTT) and incubated at 37° C. for 1 hour to remove the sulfite blocking groups from the cysteine sulfhydryls and reduce any disulfide bonds. The reaction mixture was then titrated down to pH 2.5-3.0 using concentrated formic acid.

Preparative RP-HPLC was used to purify the crude reduced hirudin. Approximately 10 to 30 mg of crude hirudin was loaded onto a 25×2.2 cm Vydac C-4 column (214TP2030, 300 angstrom pore size) equilibrated with 18% B [A=0.065% TFA (v/v); B=0.065% TFA in acetonitrile]. Elution was performed using an ascending linear gradient of 22 to 27% B at a rate of 0.1% per minute at a flow rate of 10 ml per minute. Appropriate fractions (typically greater than 95% pure), analyzed on an analytical C-4 RP-HPLC column, were pooled and freeze dried.

Hirudin was then refolded for at least 2 hours at 0.2 to 10 mg/ml in 0.1M NaHCO$_3$ (pH 10) (or for at least 6 hours in 0.1M Tris-HCl, pH 8.5), 0.5M Gnd-HCl, 1 mM EDTA and 2-20 mM oxidized glutathione (GSSG) and 1-10 mM reduced glutathione (GSH), keeping the ratio of added GSSG to GSH two to one. Refolding was monitored by analytical RP-HPLC. Refolding of hirudin leads to a decrease in the retention time on RP-HPLC (elutes at approximately 5% lower B concentrations).

Refolded hirudin was separated from unfolded hirudin and other impurities using RP-HPLC (5-30 mg per 25×2.2 cm C-4 Vydac 214TP1022, 300 angstrom). Elution was performed using an ascending linear gradient of 18 to 22% B at a rate of 0.1% per minute at a flow rate of 10 ml/minute. Appropriate fractions, analyzed by RP-HPLC as described above, were pooled and freeze dried.

All final hirudin preparations were characterized by analytical RP-HPLC, UV spectroscopy, amino acid composition and N-terminal amino acid sequence analysis and were judged to be greater than 98% pure.

EXAMPLE 4

Chemical Modification of Tyr$_3$-Substituted Hirudin Mutants

The Tyr$_3$-substituted hirudin mutants were constructed to examine whether the specificity of the chemical modification for Tyr$_{63}$ could be increased. Table 4 presents the thrombin inhibition constants for leech hirudin, wild-type r-hirudin, and the chemically modified and unmodified mutant proteins.

TABLE 4

Influence of Mutations of Position 3 and Chemical Modification of Mutants on the Inhibition Constant (Ki) of Recombinant Hirudin for Human alpha-Thrombin

| r-Hirudin Mutant | Chemical Modification | Mean Ki$^a$ (fm) | (s.d.) | [N]$^b$ |
| --- | --- | --- | --- | --- |
| rHir(Tyr$_3$) | None | 319 | (44.1) | [16] |
| rHir(Phe$_3$) | None | 126 | (12.8) | [5] |
| " | I-1 | 81 | (20.8) | [9] |
| " | I-2 | 54 | (11.0) | [7] |
| " | I-3 | 70 | (13.3) | [6] |
| " | nitration | 68 | (9.1) | [5] |
| rHir(Trp$_3$) | None | 165 | (28.4) | [5] |
| " | I-1 | 93 | (7.3) | [5] |
| " | I-2 | 66 | (21.6) | [10] |
| " | nitration | 66 | (15.5) | [10] |
| rHir(Thr$_3$) | None | 77,000$^c$ | (—) | [1] |
| rHir(VVQI$_{2-5}$) | None | 7.6 × 10$^9c$ | (—) | [1] |
| Leech | None | 98 | (17.5) | [5] |

$^a$Reaction conditions were as described in Table 2 except where noted. Results were analyzed as described in Tight-binding Inhibition Analysis.
$^b$N is the number of independent determinations.
$^c$Reaction conditions were as described in Table 2 except that S-2238 concentration was 296 uM and thrombin concentration was 2 nM.

Because each mutant has only a single reactive tyrosine (Tyr$_{63}$), nitration of both r-hirudin(Phe$_3$) and r-hirudin(Trp$_3$) produced only single homogeneous products that were readily purified by RP-HPLC. In the case of the iodination reaction which normally produces several iodinated products, the modified r-hirudin was identified because higher levels of chemical substitution caused increased retention on RP-HPLC. Upon iodination of r-hirudin(Phe$_3$) three reaction products designated I-1, I-2 and I-3 r-hirudin(Phe$_3$), in order of increasing retention time were recovered. Because tyrosine is more readily iodinated than histidine, it is possible that the I-1 and I-2 derivatives are mono- and diiodinated at tyrosine$_{63}$ and that I-3, in addition to two iodo- groups on tyrosine$_{63}$, was also iodinated on His$_{51}$. For r-hirudin(Trp$_3$) only two products, designated I-1 and I-2 r-hirudin(Trp$_3$) were observed under these conditions. However, under other conditions a third derivative of r-hirudin(Trp$_3$), I-3, was also observed but this form was not further analyzed.

Comparison of modified and wild-type r-hirudin demonstrate that both mutations caused 2 to 6-fold decreases in Ki compared to wild-type r-hirudin (t-test, $p<0.01$). The binding constant for r-hirudin (Phe$_3$) was significantly lower ($p<0.05$) than that of r-hirudin (Trp$_3$). Both iodination and nitration caused further significant decreases in the binding constants for both mutants. In the case of modified r-hirudin (Phe$_3$), the I-2 derivative bound thrombin more tightly than either the I-1 form ($p<0.01$) or the I-3 form ($p<0.05$).

Compared to the singly and multiply iodinated forms of r-hirudin (Phe$_3$), the nitrated derivative had an intermediate binding constant. These apparent differences were not statistically significant ($p>0.05$) in comparing the nitrated from with I-1 or I-3 ($p>0.05$), but the Ki of I-2 r-hirudin (Phe$_3$) was significantly lower than the nitro-r-hirudin (Phe$_3$) ($p<0.05$). For r-hirudin (Trp$_3$), the binding constants for both the I-2 and nitro-derivatives were lower than for the I-1 form ($p<0.05$), but they did not differ from one another. No differences were detected between the two mutations in r-hirudin following chemical modification of a specific type (e.g. comparing I-1 r-hirudin (Phe$_3$) to I-1 r-hirudin (Trp$_3$)).

The data presented in Table 4 demonstrates a 3.3-fold lower binding constant for leech hirudin compared to wild-type r-hirudin, which is in reasonable agreement with previous reports (Stone and Hofsteenge, (1986), supra; Dodt et al, (1988), supra). However, the binding constant for the I-2 r-hirudin (Phe$_3$) mutant is reduced approximately 2-fold ($p<0.01$) below that of leech hirudin.

Hirudin analogs with enhanced thrombin affinity may be particularly useful for therapeutic applications. It was recently shown for HV-2 that a 10-fold reduction in Ki was accompanied by a 100-fold reduction in the effective dose (ED$_{50}$) of hirudin necessary to inhibit clot formation in the rabbit Wessler venous thrombosis model (Degryse et al., (1989), supra). Thus, enhancement of hirudin affinity for thrombin is believed to magnify in vivo efficacy of the hirudin analog. An understanding of how hirudin-thrombin affinity can be modulated is important to maximize activity of other useful analogs that may have diminished activity compared to the native form.

Hirudin also has several diagnostic applications, including its use in platelet aggregation tests, in enhancing the specificity of chromogenic assays, in inhibiting fibrin formation in chromogenic assays, and in standardizing thrombin preparations. Hirudin analogs with diminished affinity may be useful in some diagnostic and therapeutic applications where it is desirable to have thrombin inhibition by hirudin more easily reversible.

Although the foregoing invention has been described in some detail by way of illustration and example, for purposes of clarity of understanding, it will be obvious that certain changes and modifications may be practiced within the scope of the appended claims.

We claim:

1. A polypeptide having hirudin activity and defined by the sequence:

$$X-AA_3-[AA_4-AA_{62}]-AA_{63}-Z$$

wherein:
- $AA_3$ is a conservative amino acid residue other than tyrosine not susceptible to electrohilic chemical modification;
- $AA_4-AA_{62}$ represent amino acids 4 through 62 of native hirudin polypeptide;
- $AA_{63}$ is a tyrosine residue or a tyrosine residue modified so as to contain an electron-withdrawing substituent at the 3- or 3-, 5-positions of the phenyl ring;
- X is hydrogen or an N-terminal extension sequence corresponding to some or all of the native hirudin polypeptide sequence; and
- Z is a hydroxyl group or a C-terminal extension sequence corresponding to some or all of the native hirudin polypeptide sequence.

2. The polypeptide of claim 1 wherein the electron-withdrawing substituent provides said tyrosine residue with a pKa in the range of about 6.5 to 8.5.

3. The polypeptide of claim 2 wherein the electron-withdrawing substituent provides said tyrosine residue with a pKa in the range of about 7 to 8.

4. The polypeptide of claim 1 wherein the electron-withdrawing substituent is selected from the group consisting of halogen and nitrate.

5. The polypeptide of claim 4 wherein the electron-withdrawing substituent is iodide.

6. The polypeptide of claim 4 wherein the electron-withdrawing substituent is fluoride.

7. The polypeptide of claim 4 wherein the electron-withdrawing substituent is nitro group.

8. The polypeptide of claim 1 wherein X is the N-terminal sequence corresponding to $valine_1$, $valine_2$, and $AA_3$ is phenylalanine or tryptophan.

9. The polypeptide of claim 1 wherein X is the N-terminal sequence corresponding to $isoleucine_1$ $threonine_2$.

10. The polypeptide of claim 1 wherein Y is the C-terminal sequence corresponding to $leucine_{64}$ $glutamine_{65}$.

11. The polypeptide of claim 1 having the amino acid sequence:

Val—Val—AA₃—Thr—Asp—Cys—Thr—Glu—Ser—Gly—Gln—Asn—
Leu—Cys—Leu—Cys—Glu—Gly—Ser—Asn—Val—Cys—Gly—Gln—Gly—Asn—Lys—
Cys—Ile—Leu—Gly—Ser—Asp—Gly—Glu—Lys—Asn—Gln—Cys—Val—
Thr—Gly—
Glu—Gly—Thr—Pro—Lys—Pro—Gln—Ser—His—Asn—Asp—Gly—Asp—Phe—Glu—
Glu—Ile—Pro—Glu—Glu—Tyr*—Leu—Glu;

wherein $AA_3$ is Phe or Trp; and
Tyr* is modified so as to contain an electron-withdrawing substituent at the 3- or 3-, 5-positions of the ring.

12. A pharmaceutical composition comprising the polypeptide of claim 1, or its physiologically tolerated salt, and a pharmaceutically acceptable carrier.

13. A method for treating thrombotic conditions in mammals, which comprises administering to a mammal in need of such treatment, an effective amount of the pharmaceutical composition of claim 12.

* * * * *